(12) United States Patent
Moreton

(10) Patent No.: US 6,200,936 B1
(45) Date of Patent: Mar. 13, 2001

(54) SALICYCLIC CALIXARENES AND THEIR USE AS LUBRICANT ADDITIVES

(75) Inventor: David John Moreton, East Yorkshire (GB)

(73) Assignee: The Lubrizol Corporation, Wickliffe, OH (US)

( * ) Notice: Subject to any disclaimer, the term of this patent is extended or adjusted under 35 U.S.C. 154(b) by 0 days.

(21) Appl. No.: 09/308,872
(22) PCT Filed: Nov. 12, 1998
(86) PCT No.: PCT/GB98/03398
  § 371 Date: May 26, 1999
  § 102(e) Date: May 26, 1999
(87) PCT Pub. No.: WO99/25677
  PCT Pub. Date: May 27, 1999

(30) Foreign Application Priority Data

Nov. 13, 1997 (GB) .................................... 9723888
Jul. 25, 1998 (GB) .................................... 9816162

(51) Int. Cl.$^7$ .............................................. C10M 129/14
(52) U.S. Cl. ..................... 508/479; 508/331; 508/510; 44/389; 44/386; 44/403
(58) Field of Search .................... 508/460, 300, 508/479, 502, 510, 518, 331; 44/329, 398, 400, 389, 386, 403; 560/57, 70, 71; 562/468, 476, 477

(56) References Cited

U.S. PATENT DOCUMENTS

| | | | |
|---|---|---|---|
| 4,617,336 | * 10/1986 | Pastor et al. ............... | 524/291 |
| 5,114,601 | * 5/1992 | Cook et al. ................ | 252/25 |
| 5,205,946 | * 4/1993 | Cook et al. ................ | 252/25 |
| 5,434,208 | * 7/1995 | Batelaan et al. ............ | 524/288 |
| 5,589,445 | * 12/1996 | Leahy et al. ............... | 508/381 |
| 5,602,084 | * 2/1997 | Moreton ................... | 508/391 |
| 5,780,403 | * 7/1998 | Moreton ................... | 508/580 |
| 5,840,814 | * 11/1998 | Majoros et al. ............. | 525/502 |
| 5,881,358 | * 3/1999 | Miyano et al. .............. | 423/8 |

FOREIGN PATENT DOCUMENTS 0450874 10/1991 (EP) .
0708171 4/1996 (EP) .

OTHER PUBLICATIONS

International Search Report for PCT Application No. PCT/GB98/03398; Mailed on Feb. 23, 1999.
Schneider et al.; Chem. Ber. 1994, 127, pp. 2455–2469; "Synthese and Eigenschaften Von Makrocyclen Aus Resorcinen Sowie Von Entsprechenden Derivaten Und Wirt–Gast– Komplexen".

* cited by examiner

Primary Examiner—Jerry D. Johnson
(74) Attorney, Agent, or Firm—Michael F. Esposito

(57) ABSTRACT

This invention relates to a cyclic compound comprising m units of formula (Ia)

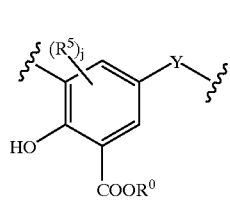

(Ia)

and n units of the formula (Ib)

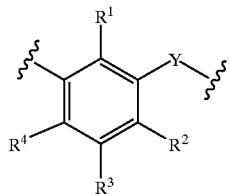

(Ib)

joined together to form a ring, wherein each Y is a divalent bridging group which may be the same or different in each unit; $R^0$ is H or an alkyl group of 1 to 6 carbon atoms; $R^5$ is H or an alkyl group of 1 to 60 carbon atoms; j is 1 or 2; $R^3$ is hydrogen, a hydrocarbyl or a hetero-substituted hydorcarbyl group; either $R^1$ is hydroxy and $R^2$ and $R^4$ are independently either hydrogen, hydrocarbyl or hetero-substituted hydrocarbyl, or $R^2$ and $R^4$ are hydroxyl and $R^1$ is either hydrogen, hydrocarbyl or hetero-substituted hydrocarbyl; m is from 1 to 8; n is at least 3, and m +n is 4 to 20. This invention also relates to metal salts of the foregoing compound, especially overbased metal salts. The invention also relates to additive compositions, finished lubricating oil compositions and fuel compositions containing the foregoing compound or metal salt thereof. The invention also relates to a process for making the foregoing compound and salts thereof.

11 Claims, 1 Drawing Sheet

SALICYCLIC CALIXARENES AND THEIR USE AS LUBRICANT ADDITIVES

TECHNICAL FIELD

This invention relates to cyclic compounds. More particularly, this invention relates to calixarenes containing within the calixarene ring at least one unit of salicylic acid, and to lubricating oil compositions and fuel compositions containing such compounds or metal salts thereof. The inventive compounds are particularly suitable for use in lubricating oil compositions for medium- or low-speed diesel engines, especially four-stroke trunk-piston engines.

BACKGROUND OF THE INVENTION

Lubricating oils for medium- or low-speed diesel engines typically contain a range of additives which perform a variety of functions: for example they may comprise dispersants to minimise deposit formation in various parts of the engine or detergent additives. Contamination of these lubricating oil compositions with unburnt residual fuel oil is a problem recognised in the industry. This leads to severe engine cleanliness problems in service which is sometimes referred to as "black paint." The problem is particularly widespread in 4-stroke trunk-piston engines where dirty cam boxes and crankcases are encountered. However, the problem is not confined to 4-stroke engines; 2-stroke cross-head engines may also suffer from the problem. These 2-stroke engines typically use two separate lubricating oils, one for the crankcase and one for the cylinder, but it is in the crankcase where the heavy deposits typically occur. It might be expected that the problem would be overcome simply by using more of the conventional dispersant additive in the lubricating oil, but this measure has met with very limited success.

Acidity in lubricating oil is another long-recognised problem. In the operation of the internal combustion engine by-products from the combustion chamber often blow by the piston and admix with the lubricating oil. Additives are generally employed to neutralise the acidic materials and disperse sludge within the lubricating oil. Examples are overbased alkaline earth metal sulphurised hydrocarbyl-substituted phenates, salicylates, napthenates and sulphonates. Overbased calixarates are also known as detergent additives for lubricating oils, eg EP-A-450874. The term "overbased" is generally used to describe those metal salts in which the ratio of the number of equivalents of the metal moiety to the number of equivalents of the acid moiety is greater than one, and is usually greater than 1.2 and may be as high as 4.5 or greater. In contrast, the equivalent ratio of a metal moiety to acid moiety in "normal" or "neutral" metal salts is one, and in "low-based" salts is less than one. Thus, the overbased material usually contains greater than 20% in excess of the metal present in the corresponding neutral material. For this reason overbased alkaline earth metal hydrocarbyl-substituted salts have a greater capability for neutralising acidic matter than do the corresponding neutral alkaline earth metal hydrocarbyl-substituted salts, though not necessarily an increased detergency power. The degree of overbasing is expressed as "Total Base Number" or TBN, which is also sometimes referred to as Alkalinity Value or AV, and is measured by the method of ASTM D2896.

EP-A-708171 discloses linear molecules comprising optionally substituted phenol units linked by alkylene bridges, with one end of the chain similarly linked to a salicylate moiety. The number of aromatic units thus linked is said generally not to exceed 4, or preferably 3. Overbased metal salts of these compounds are disclosed as being useful as detergents or dispersants, particularly in respect of asphaltene compounds, which are responsible for black paint.

With the present invention the problem of black paint is substantially reduced or eliminated by including in the lubricating oil novel calixarene compounds which contain within the calixarene ring at least one salicylic acid unit. Overbased metal salts of these compounds also function as high TBN detergents, thereby providing two functions in one product. Furthermore, the performance of conventional gasoline and diesel detergents/dispersants is enhanced by combining them with such compounds.

SUMMARY OF THE INVENTION

This invention relates to a cyclic compound comprising m units of formula (Ia)

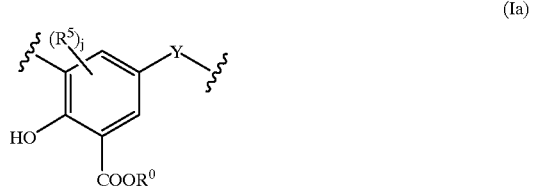

(Ia)

and n units of formula (Ib)

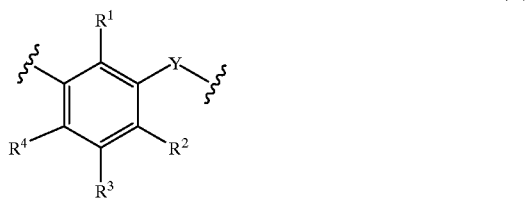

(Ib)

joined together to form a ring, wherein each Y is a divalent bridging group which may be the same or different in each unit; $R^0$ is H or an alkyl group of 1 to 6 carbon atoms; $R^5$ is H or an alkyl group of 1 to 60 carbon atoms; and j is 1 or 2; $R^3$ is hydrogen, a hydrocarbyl or a hetero-substituted hydorcarbyl group; either $R^1$ is hydroxy and $R^2$ and $R^4$ are independently either hydrogen, hydrocarbyl or hetero-substituted hydrocarbyl, or $R^2$ and $R^4$ are hydroxyl and $R^1$ is either hydrogen, hydrocarbyl or hetero-substituted hydrocarbyl; m is from 1 to 8; n is at least 3, and m+n is 4 to 20. This invention also relates to metal salts of the foregoing compound, especially overbased metal salts. The invention also relates to additive compositions, finished lubricating oil compositions and fuel compositions containing the foregoing compound or metal salt thereof. The invention also relates to a process for making the foregoing compound and metal salt thereof.

DETAILED DESCRIPTION OF THE PREFERRED EMBODIMENT

Figure 1:
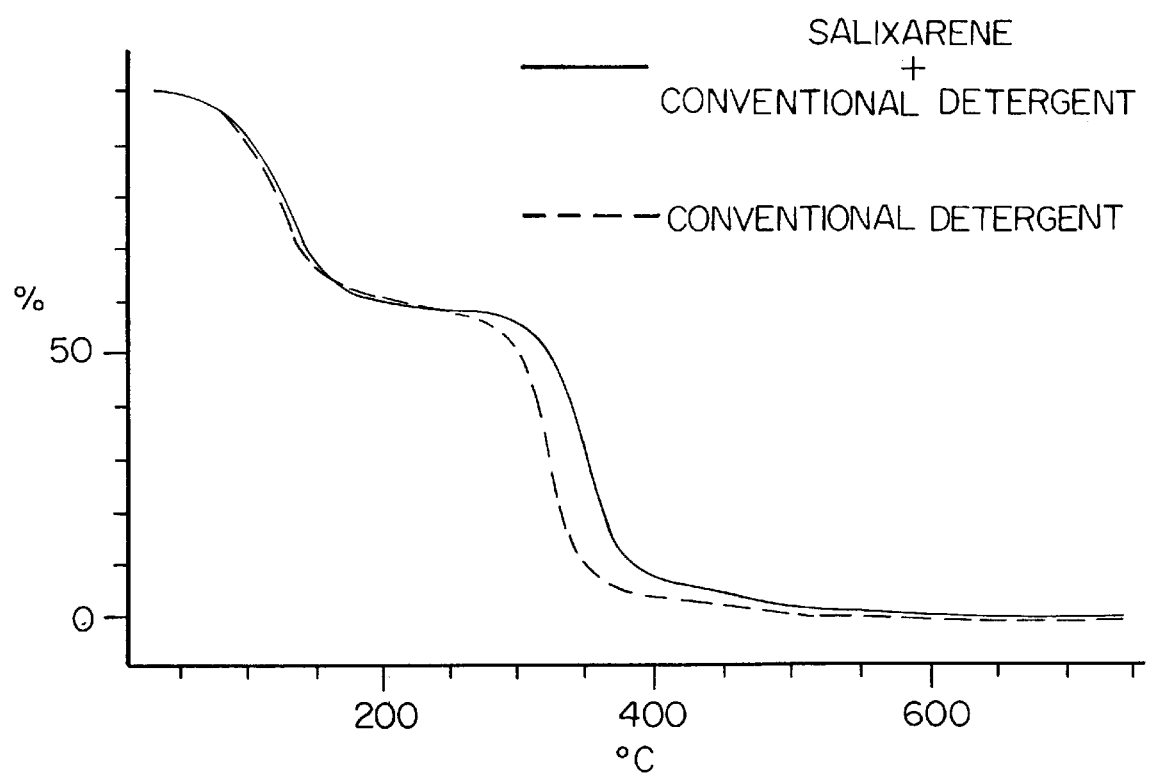
FIG. 1 is a plot disclosing the thermogravimetric analysis of two test samples from Example 3.

In a first aspect the present invention provides a cyclic compound comprising m units of the formula (Ia)

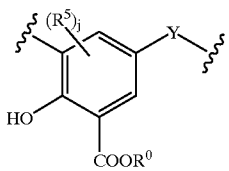

(Ia)

and n units of the formula (Ib)

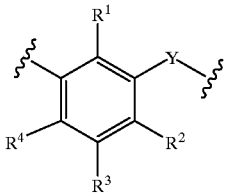

(Ib)

joined together to form a ring, wherein each Y is a divalent bridging group which may be the same or different in each unit; $R^0$ is H or an alkyl group of 1 to 6 carbon atoms; $R^5$ is H or an alkyl group of 1 to 60 carbon atoms; j is 1 or 2; $R^3$ is hydrogen, a hydrocarbyl or a hetero-substituted, hydorcarbyl group; either $R^1$ is hydroxy and $R^2$ and $R^4$ are independently either hydrogen, hydrocarbyl or heterosubstituted hydrocarbyl, or $R^2$ and $R^4$ are hydroxyl and $R^1$ is either hydrogen, hydrocarbyl or hetero-substituted hydrocarbyl; m is from 1 to 8; n is at least 3; and m+n is 4 to 20.

When more than one salicylic acid unit is present in the ring (ie m>1), the salicylic acid units (formula (Ia)) and phenol units (formula (Ib)) are distributed randomly, although this does not exclude the possibility that in some rings there may be several salicylic acid units joined together in a row.

Each Y may independently be represented by the formula $(CHR^6)_d$ in which $R^6$ is either hydrogen or hydrocarbyl and d is an integer which is at least 1. In one embodiment, $R^6$ contains 1 to 6 carbon atoms, and in one embodiment it is methyl. In one embodiment, d is from 1 to 4. Y may optionally be sulphur rather than $(CHR^6)_d$ in up to 50% of the units, such that the amount of sulphur incorporated in the molecule is up to 50 mole %. In one embodiment, the amount of sulphur is between 8 and 20 mole %, and in one embodiment the compound is sulphur-free.

Regarding $R^1$ to $R^6$, the term "hydrocarbyl" includes $(C_1-C_{60})$ alkyl such as t-butyl, t-amyl, s-butyl, isopropyl, octyl, nonyl, dodecyl and octadecyl. Alternatively the hydrocarbyl group may be derived from a polyolefin, for example polyethylene, polypropylene, polybutylene or a polyolefin copolymer, for example an ethylene/propylene copolymer, preferably derived from a polyisobutene. Examples include dodecyl and octadecyl. Alternatives include isoprene-butadiene, styrene-isoprene or styrene-butadiene block copolymers such as those disclosed in WO 96/40846, or ethylene-propylene and ethylene-butene-1 copolymers having molecular weights from 1500 to 2500 or 7500, as disclosed in U.S. Pat. No. 5,567,344 and U.S. Pat. No. 5,578,237. Mixtures of all the above may also be employed. Any hetero-substituted hydrocarbyl group has the heteroatom, preferably —O— or =NH, interrupting a chain of carbon atoms, such as an alkoxy-alkyl group of 2–20 carbons.

For convenience the compounds of the invention are somtimes hereinafter referred to as "salixarenes" and their metal salts as "salixarates".

In one embodiment, Y is $CH_2$; $R^1$ is hydroxyl; $R^2$ and $R^4$ are independently either hydrogen, hydrocarbyl or heterosubstituted hydrocarbyl; $R^3$ is either hydrocarbyl or heterosubstituted hydrocarbyl; $R^0$ is H; $R^5$ is an alkyl group of 6 to 50 carbon atoms, and in one embodiment 4 to 40 carbon atoms, and in one embodiment 6 to 25 carbon atoms; and m+n has a value of at least 5, and in one embodiment at least 6, and in one embodiment at least 8, where m is 1 or 2, and in one embodiment m is 1.

In one embodiment, $R^2$ and $R^4$ are hydrogen; $R^3$ is hydrocarbyl, and in one embodiment alkyl of greater than 4 carbon atoms, and in one embodiment greater than 9 carbon atoms; $R^5$ is hydrogen; and m+n is from 6 to 12; m is 1 or 2. A particularly preferred salixarene is dodecyl-salicylic calix[8]arene, which has the structure.

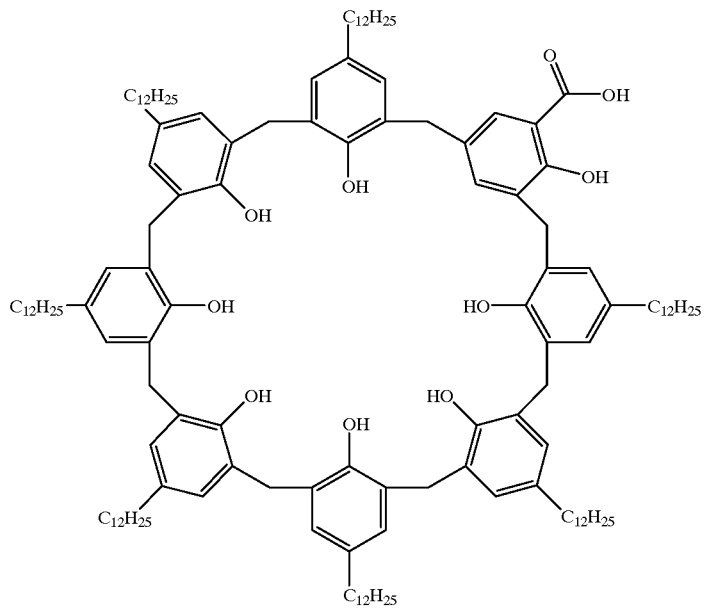

In one embodiment, the compound of the invention is the same as the foregoing except that it has two salicylic acid units rather than one in an 8-unit ring as above.

For a review of calixarenes the reader is referred to 'Monographs in Supramolecular Chemistry' by C David Gutsche, Series Editor—J Fraser Stoddart, published by the Royal Society of Chemistry, 1989. Calixarenes having a substituent hydroxyl group or groups include homocalixarenes, oxacalixarenes, homooxacalixarenes and heterocalixarenes.

The salixarenes of the invention may be made by reacting together in appropriate amounts an optionally substituted salicylic acid, a substituted phenol, and an aldehyde, optionally in the presence of sulphur.

Accordingly a further aspect of the invention comprises a process for producing the foregoing salixarenes comprising reacting together in a solvent (e.g., 50 weight % dilution or greater), in the presence of a basic catalyst, compounds of the formulas (IIa) and (IIb)

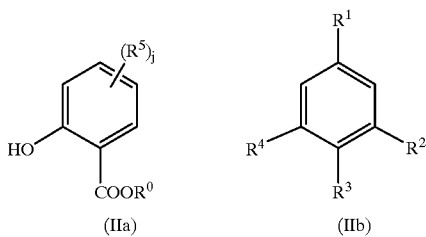

with an aldehyde of the formula $O=CHR^6$, and optionally sulphur; where $R^0$ to $R^6$ and j are as defined previously. By "50 weight % dilution" is meant that the solvent comprises at least 50% by weight of the reaction solution once all the reactants have been added. In one embodiment, the solvent comprises at least 80% by weight, and in one embodiment at least 90% by weight of the reaction solution.

The basic catalysts are alkali metal hydroxides such as sodium hydroxide, potassium hydroxide and lithium hydroxide. Sodium hydroxide is preferred.

High dilution of the reaction mixture is necessary in order to ensure the formation of rings rather than linear molecules. At dilutions well below 50% by weight only linear molecules are formed. However even at high dilutions a proportion of the product may comprise linear molecules. Linear molecules are composed of units having formulas (Ia) and (Ib) except that instead of the ends of the molecule being joined to form a ring, each end has a terminal group which is independently one of the following:

(III)

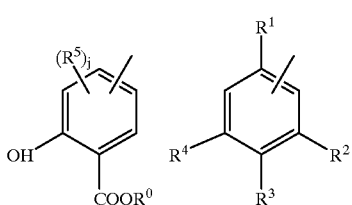

In the linear molecule the total number of units m+n is from 2 to 20, m is from 1 to 8 and n is at least 1. In one embodiment of the invention, compounds of the formulas (IIa) and (IIb) above are reacted with an aldehyde of the formula $O=CHR^6$, and optionally sulphur; where $R^0$ to $R^6$ are as defined previously, which reaction product comprises at least 20% by weight of a cyclic compound comprising units of formulas (Ia) and (Ib) and no more than 80% of the linear version of said compound. In one embodiment, the cyclic form comprises at least 40% by weight, and in one embodiment at least 60% and most preferably at least 80% by weight of the reaction product. Good performance against black paint is achieved by use of the cyclic salixarenes, and hence the compositions of the invention, although they may contain a mixture of both cyclic and linear forms, are preferred to contain as much of the cyclic form as possible.

The salixarenes of the invention may be reacted with a metal base to provide salixarates, which may be low-based, neutral or overbased. Accordingly, another aspect of the invention provides a neutral, low-based or overbased metal salt of a salixarene as defined above having a substituent hydroxyl group or groups available for reaction with a metal base.

In one embodiment of the invention, a process for making low based or neutral salixarates is provided. The process comprises the steps of:

(I) forming a mixture of components (A) and (C);

component (A) comprising either (i) a salixarene having at least one substituent hydroxyl group available for reaction with a metal base or (ii) a low-based or neutral metal salt of a salixarene derived from a salixarene having at least one substituent hydroxyl group available for reaction with said metal base, component (C) comprising a solvent comprising either component ($C_1$) or ($C_2$);

component ($C_1$) comprising either (i) a polyhydric alcohol having 2 to 4 carbon atoms, (ii) a di-($C_3$ or $C_4$) glycol, (iii) a tri-($C_2$–$C_4$) glycol or (iv) a mono- or poly-alkylene glycol alkyl ether of the formula:

$$R^9(OR^{10})_fOR^{11} \qquad (IV)$$

wherein in the formula (IV) $R^9$ is a $C_1$ to $C_6$ alkyl group, $R^{10}$ is an alkylene group of 1 to 6 carbon atoms, $R^{11}$ is hydrogen or a $C_1$ to $C_8$ alkyl group, and f is an integer from 1 to 6;

component ($C_2$) comprising a $C_1$ to $C_4$ monohydric alcohol in combination with a hydrocarbon solvent; and (II) adding a metal base (B) to the mixture of components (A) and (C), the addition of said metal base (B) to said mixture of (A) and (C) being in a single addition or in a plurality of additions, steps (I) and (II) being performed concurrently or sequentially.

In one embodiment, component ($C_1$) further comprises: (a) a hydrocarbon solvent; or (b) either (i) water, (ii) a $C_1$ to $C_{20}$ monohydric alcohol, (iii) a ketone having up to 20 carbon atoms, (iv) a carboxylic ester having up to 10 carbon atoms, (v) an aliphatic, alicyclic or aromatic ether having up to 20 carbon atoms, or a mixture of two or more of (i) to (v).

In one embodiment, the invention includes a process for the production of overbased salixarates which comprises the foregoing process for making a low based or neutral salixarate but with the addition of:

(III) adding (D) carbon dioxide to the mixture of components (A), (B) and (C) subsequent to each addition of component (B).

Component (A) may be either (i) a salixarene having a substituent hydroxyl group or groups available for reaction with a metal base or (ii) a low-based, neutral or overbased salixarate derived from such salixarene. Pre-formed salixarates wherein the equivalent ratio of metal base moiety to salixarene is either 1 (neutral salixarates) or less than 1 (low-based salixarates) may be employed to produce the desired overbased salixarates. Alternatively, overbased salixarates (iii) may be employed, in which case the resulting overbased product is a salixarate having an increased degree of overbasing, i.e. a higher alkalinity value or higher TBN.

In addition to one of the alternatives (i) to (iii), component (A) may further include a compound of the formula (III) above, which is a linear form of the compound of formula (I).

Component (B) is a metal base. The metal moiety may be any alkali or alkaline earth metal, preferably is an alkaline earth metal. The metal may be calcium, magnesium or barium, and in one embodiment it is calcium. The base moiety may be an oxide or a hydroxide, preferably hydroxide. A calcium base may be added, for example, in the form of quick lime (CaO) or in the form of slaked lime ($Ca(OH)_2$) or mixtures of the two in any proportion. Component (B) may be added in whole to the initial reactants or in part to the initial reactants and the remainder in one or more further additions at intermediate points during the reaction.

Component (C) is a solvent for the reactants. The solvent (C) may be either ($C_1$) optionally in combination with either (a) or (b), or ($C_2$). Component ($C_1$) is either (i) a polyhydric alcohol having 2 to 4 carbon atoms, (ii) a di-($C_3$ or $C_4$) glycol, (iii) a tri-($C_2$ to $C_4$) glycol or (iv) a mono- or poly-alkylene glycol alkyl ether of the formula:

$$R^9(OR^{10})_fOR^{11} \tag{IV}$$

wherein in formula (IV), $R^9$ is a $C_1$ to $C_6$ alkyl group, $R^{10}$ is an alkylene group, $R^{11}$ is hydrogen or a $C_1$ to $C_6$ alkyl group, and f is an integer from 1 to 6. Examples of compounds represented by formula (IV) include the monomethyl or dimethyl ethers of (a) ethylene glycol, (b) diethylene glycol, (c) triethylene glycol or (d) tetraethylene glycol. A useful compound is methyl diglycol ($CH_3OCH_2CH_2OCH_2CH_2OH$). Mixtures of glycol ethers and glycols may also be employed. The polyhydric alcohol may be either a dihydric alcohol, for example ethylene glycol or propylene glycol, or a trihydric alcohol, for example glycerol. The di-($C_3$ or $C_4$) glycol may be dipropylene glycol, the tri-($C_2$ to $C_4$) glycol may be triethylene glycol. In one embodiment, component ($C_1$) is either ethylene glycol or methyl diglycol.

Component (a) is a hydrocarbon solvent which may be aliphatic or aromatic. Examples of suitable hydrocarbons include toluene, xylene, naphtha and aliphatic paraffins, for example hexane, and cycloaliphatic paraffins.

Component (b) may be any one or more of either (i) water, (ii) a $C_1$ to $C_{20}$ monohydric alcohol, (iii) a ketone having up to 20 carbon atoms, (iv) a carboxylic acid ester having up to 10 carbon atoms or (v) an aliphatic, alicyclic or aromatic ether having up to 20 carbon atoms. Examples include methanol, 2-ethyl hexanol, cyclohexanol, cyclohexanone, benzyl alcohol, ethyl acetate and acetophenone.

Component ($C_2$) may be a $C_1$ to $C_4$ monohydric alcohol, preferably methanol, in combination with a hydrocarbon solvent. The hydrocarbon solvent may be any of those referred to above as being useful of Component (a). The hydrocarbon solvent is preferably toluene.

Useful solvents (C) include ethylene glycol, a mixture of ethylene glycol and 2-ethyl hexanol, and a mixture of methanol and toluene.

Generally, in view of the intended use of the product, it is preferred to incorporate a lubricating oil as a supplemental solvent. The lubricating oil may be an animal, vegetable or mineral oil. The lubricating oil may be a petroleum derived lubricating oil, such as a naphthenic base, paraffin base or mixed base oil. Solvent neutral oils are suitable. Alternatively, the lubricating oil may be a synthetic lubricating oil. Suitable synthetic lubricating oils include synthetic ester lubricating oils, which oils include diesters such as di-octyl adipate, di-octyl sebacate and tri-decyladipate, or polymeric hydrocarbon lubricating oils, for example liquid polyisobutenes and poly-alpha olefins.

Component (D) is carbon dioxide, added subsequent to each addition of component (B). Carbon dioxide may be added in the form of a gas or a solid, preferably in the form of a gas. In gaseous form it may be blown through the reaction mixture.

The weight ratio of component (A) to component (C) is from 10 to 65 parts by weight of (A) per 100 parts by weight of (C), and in one embodiment about 20 to about 60 parts by weight of (A) per 100 parts by weight of (C). The ratio of mole equivalents of component (B) to mole equivalents of component (A) is generally from 0.05 to 20 mole equivalents of (B) per mole equivalent of (A), and in one embodiment 0.08 to 18 mole equivalents of (B) per mole equivalent of (A). The ratio of the number of moles of metal in component (B) to the number of moles of carbon dioxide in (D) is from 0.3 to 1.6 moles of metal in (B) per mole of carbon dioxide in (D), and in one embodiment 0.55 to 1.3 moles of metal in (B) per mole of carbon dioxide in (D).

In one embodiment, the reaction mixture may include component (E). Component (E) is either (i) a carboxylic acid containing from 6 to 100 carbon atoms or an anhydride thereof, (ii) a di- or polycarboxylic acid containing from 36 to 100 carbon atoms or an anhydride thereof, (iii) a hydrocarbyl-substituted sulphonic acid or an anhydride thereof, (iv) a hydrocarbyl-substituted salicylic acid or an anhydride thereof, (v) a hydrocarbyl-substituted naphthenic acid or an anhydride thereof, (vi) a hydrocarbyl-substituted phenol or (vii) a mixture of any two of (i) to (vi). Of the aforesaid alternatives Component (E) is preferably (i). Component (E) may be added during step (I), (II) or (III), or prior to or subsequent to any of the foregoing steps. In one embodiment, component (E) is added during step (I). When component (E) is used, it is typically used in an amount of up to 40% by weight based on the combined weight of components (A), (B), (C), (D) and (E), and one embodiment from 2 to 38% by weight, and in one embodiment from 12 to 27% by weight. Component (i) of component (E) may be an acid having the formula:

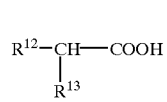

(V)

wherein in formula (V), $R^{12}$ is a $C_{10}$ to $C_{24}$ alkyl or alkenyl group, and $R^{13}$ is either hydrogen, a $C_1$ to $C_4$ alkyl group or a $-CH_2COOH$ group. Preferably, $R^{12}$ in formula (V) is an unbranched alkyl or alkenyl group. Preferred acids of formula (V) are those wherein $R^{13}$ is hydrogen and $R^{12}$ is a $C_{10}$ to $C_{24}$, more preferably $C_{18}$ to $C_{24}$ unbranched alkyl group.

Examples of saturated carboxylic acids represented by formula (V) include capric, lauric, myristic, palmitic, stearic, isostearic, arachidic, behenic and lignoceric acids. Examples of unsaturated acids formula (V) include lauroleic, myristoleic, palmitoleic, oleic, gadoleic, erucic, ricinoleic, linoleic and linolenic acids. Mixtures of any of the foregoing acids may also be employed, for example, rape top fatty acids. Particularly suitable mixtures of acids are those commercial grades containing a range of acids, including both saturated and unsaturated acids. Such mixtures may be obtained synthetically or may be derived from natural products, for example, tall, cotton, ground nut, coconut, linseed, palm kernel, olive, palm, castor, soyabean, sunflower, herring and sardine oils and tallow.

Instead of, or in addition to, the foregoing carboxylic acids, component (E) may be an acid anhydride, acid chloride or the ester derivative of any of the foregoing acids, and of these the acid anhydride is preferred. It is preferred, however, to use a carboxylic acid or a mixture of carboxylic acids. A preferred carboxylic acid of formula (V) is stearic acid. While not wishing to be bound by theory, it is believed that component (E) when present, chemically modifies the overbased salixarate product.

As regards component (ii) of component (E), this is preferably a polyisobutylene substituted succinic acid or a polyisobutylene substituted succinic anhydride. The molecular weight of such acid or anhydride is typically in the range of 300 to 3000, and in one embodiment 700 to 1300.

As regards to components (iii), (iv), (v) and (vi) of component (E), the hydrocarbyl substituent may contain up to 125 aliphatic carbon atoms, and in one embodiment 6 to 20 carbon atoms. Examples of suitable substituents include alkyl groups, for example hexyl, cyclohexyl, octyl, isoctyl, decyl, tridecyl, hexadecyl, eicosyl and tricosyl. Hydrocarbyl groups derived from the polymerisation of both terminal and internal olefins, for example ethene, propene, 1-butene, isobutene, 1-hexene, 1-octene, 2-butene, 2-pentene, 3-pentene and 4-octene can be used. In one embodiment, the hydrocarbyl substituent is derived from polypropylene, poly-1-butene or polyisobutylene, preferably polyisobutylene.

The reaction mixture may also include as component (F) a catalyst (or promoter) for the reaction. The catalyst may be an organic compound or an inorganic compound. The catalyst (F) is added during step (I), (II) or (III), or prior to or subsequent to any of the foregoing steps. In one embodiment, the catalyst (F) is added during step (I). When component (F) is used, the amount of component (F), added to the mixture of (A), (B), (C), (D) and optionally (E) ranges from 0.1% to 3% by weight based on the combined weight of the mixture, and in one embodiment 2% by weight. Suitable organic compounds include (i) organic halides (e.g., chlorides, bromides, iodides) or (ii) organic alkanoates, which may be represented by the formula:

$$R^{14}\text{—}X \qquad (VI)$$

wherein in the formula (VI), $R^{14}$ is either an alkyl, aryl or alkaryl group preferably having 3 to 20, or 6 to 20, or 7 to 20 carbons, respectively, or a halo-derivative thereof. X is either halogen, suitably chlorine, bromine or iodine, preferably chlorine, or the group $OCOR^{15}$ wherein $R^{15}$ is $C_1$ to $C_4$ alkyl. Alternatively, the organic halide may be an HX salt of an organic base, for example guanidine hydrochloride. An example of an organic halide represented by formula (VI) is octyl chloride. Mixtures of (i) and (ii) of component (F) may also be employed. Suitable inorganic compound catalysts include inorganic halides, particularly inorganic chlorides, and inorganic alkanoates. Examples of suitable inorganic compound catalysts include calcium acetate, calcium chloride, ammonium chloride, ammonium acetate, aluminum chloride and zinc chloride, of which calcium chloride and calcium acetate are preferred. Provided that the catalyst is present during the carbonation step (i.e., step (III)), it may be added at any point in the process, though it is usually convenient to add the catalyst initially during step (I).

In order to produce an overbased salixarate from component (A)(i) or (A)(ii) it is necessary only to react component (A) with components (B), (C) and (D), using the appropriate proportions of components (A) and (B) to achieve overbasing. Suitably component (B) may be added in one or more additions, preferably in a single addition.

In order to produce a high TBN overbased salixarate there may be employed an overbased metal salixarate derived from a salixarene having a substituent group or groups available for reaction, and it is preferred to employ component (E), particularly either (E)(i) or (ii), and more particularly stearic acid, while at the same time adjusting the relative amounts of components (A) and (B) to a value sufficient to produce the desired high TBN salixarate.

The temperature at which the process is operated may be a temperature in the range from 15 to 200° C., and in one embodiment from 50 to 175° C. The selection of the optimum temperature within the aforesaid range is dependent in part on the nature of the solvent employed.

Generally, the process is operated in the presence of a lubricating oil. At the conclusion of the process it is preferred to recover the salt as a solution in lubricating oil by separating off volatile fractions, for example, by distillation at subatmospheric pressure. Finally, it is preferred to filter the solution. Alternatively, the solution may be centrifuged.

Salixarates produced by the above process may have TBNs of 100 mg KOH/g or below (i.e., low based or neutral salixarates). In one embodiment, the salixarates are overbased, in which case they generally have TBNs of at least 200 mg KOH/g, and in one embodiment from 200 to 500 mg KOH/g, and in one embodiment from 300 to 500 mg KOH/g, and in one embodiment from 400 to 500 mg KOHlg. The salixarates are generally employed in the form of a concentrate in lubricating oil, which is a further aspect of the present invention. Such concentrates may themselves be incorporated into an additive package for addition to the lubricating oil used in the engine.

The lubricating oil compositions of the present invention are suitable for use in either a low- or medium-speed engines especially marine diesel engines. Typically such engines are 4-stroke trunk piston engines having an engine speed of 50–1,000 rpm, and in one embodiment 100–500 rpm, and a brake horse-power (BHP) per cylinder of 10–3,000, and in one embodiment 250–2,000. The engine can also be a 2-stroke cross-head engine having a speed of 40–1,000 rpm, and in one embodiment 100–500, rpm and a BHP per cylinder of 100–8,000.

In a further aspect of the present invention there is provided a method of reducing deposits in a low- or medium-speed diesel engine, comprising lubricating the moving parts of the engine with the above-defined lubricating oil composition.

The lubricating oil compositions of the present invention have a TBN in the range from 0.1 to 100 mg KOH/g. Where the composition is to be used in a 4-stroke trunk piston engine the TBN is preferably in the range from 5 to 70, more preferably from 8 to 50 mg KOH/g. When it is to be used in a 2-stroke cross-head engine and particularly for the crankcase, the TBN of the composition is preferably in the range from 0.1 to 15, more preferably in the range from 1 to 10 mg KOH/g.

The lubricating oil compositions of the present invention are typically monograde lubricants (i.e. lubricants which exhibit little or no viscosity index improvement properties, e.g. an SAE 30 oil). The oil itself may be any oil suitable for the lubrication of a low- or medium-speed diesel engine, particularly a marine diesel engine. It may be an animal, a vegetable or a mineral oil. In one embodiment, it is a petroleum-derived lubricating oil, such as a naphthenic base, paraffin base or mixed base oil. Alternatively, it may be a synthetic lubricating oil. Useful synthetic lubricating oils include synthetic ester lubricating oils, which oils include diesters such as di-octyl adipate, di-octyl sebacate and tri-decyl adipate, or polymeric hydrocarbon lubricating oils, for example liquid polyisobutene and poly-alpha olefins. In one embodiment, a mineral oil is employed. The oil may be suitable for lubricating a low- or medium-speed marine diesel engine without adjustment of its viscosity. If viscosity adjustment is required it may be achieved by the addition of, for example, bright stock. The lubricating oil typically comprises greater than 70% by weight, and in one emboidment greater than 80% by weight of the inventive lubricating oil composition.

The inventive lubricating oil composition may be contaminated with a fuel oil which has a residual oil content. These fuel oils are suitable for use as diesel fuel oils. Fuel oils can in general be divided into two main categories, namely, distillates and heavy fuels. Distillates consist of one or more distilled fractions. Heavy fuels are fuels which comprise at (east a proportion of a residual oil, that is an oil which remains after the distilled fractions have been removed from an unrefined oil. The composition of the residual oil will vary with the composition of the starting oil which is usually a crude oil and will also vary depending upon the distillation conditions. However, by its nature residual oil is of high molecular weight and high boiling point. Heavy fuels can also comprise, in addition to residual oil, distillates. However, heavy fuels generally comprise at least 90% by weight, and in one embodiment at least 95% by weight, and in one embodiment at least 99% by weight residual oil. In one embodiment, the present invention relates to lubricating oil compositions that are contaminated with a heavy fuel. The amount of heavy fuel in the lubricating oil composition will vary. Typically the lubricating oil composition comprises between 0.1 to 25% by weight, and in one embodiment 0.1 to 10% by weight, and in one embodiment 0.3 to 5% by weight, and in one embodiment, 0.5 to 3% by weight heavy fuel oil, which as defined above is a fuel oil which has a residual oil content.

The lubricating oil compositions of the invention typically contain at least 0.01% by weight of the inventive salixarene or salixarate, and in one one embodiment at least 0.05% by weight, and in one embodiment at least 0.1% by weight. The lubricating oil compositions of the invention typically contain 5 to 95% by weight of the inventive salixarenes or salixarates, and in one embodiment 25 to 55% by weight.

In addition to the lubricating oil and the salixarenes or salixarates of the invention, the inventive lubricating oil compositions may contain other additives, particularly dispersants. Although any type of dispersant may be employed in the composition, a suitable dispersant is one derived from a hydrocarbyl-substituted succinic acid or anhydride by reaction with an amine i.e. a hydrocarbyl-substituted succinimide, e.g. a polyisobutylene substituted succinimide. These succinimides are well known in the art. Succinimide production is described in, for example, U.S. Pat. No. 2,992,708; U.S. Pat. No. 3,018,291; U.S. Pat. No. 3,024,237; U.S. Pat. No. 3,100,673; U.S. Pat. No. 3,219,666; U.S. Pat. No. 3,172,892 and U.S. Pat. No. 3,272,746. Succinimide dispersants which are mono- or bis-succinimides may be employed.

The amount of dispersant present in the low- or medium-speed diesel engine lubricating oil composition of the present invention may be in the range from 0.01 to 5% by weight, and in one embodiment from 0.1 to 2.5% by weight based on the weight of the lubricating oil composition.

In one embodiment, the inventive lubricating oil composition comprises: from 0 to 5% by weight, and in one embodiment from 0.1% to 3% by weight of a hydrocarbyl-substituted succinimide dispersant; from 0.05 to 5% by weight, and in one embodiment from 0.1% to 3% of a salixarene or salixarate of the invention; and a low- or medium-speed diesel engine lubricating oil.

In addition to the foregoing, the inventive lubricating oil composition may contain one or more additives conventionally employed in low- or medium-speed diesel engine lubricating oil compositions. Examples of such additives include additional detergents, foam inhibitors, extreme pressure/antiwear agents, rust inhibitors, antioxidants, and the like. The additional detergents that can be employed in the include hydrocarbyl-substituted alkaline earth metal phenates, salicylates, naphthenates, sulphonates or carboxylates, which may be neutral or overbased materials.

The lubricating oil composition of the invention may be prepared by diluting a concentrate comprising a solution of the salixarene or salixarate of the invention and optionally other useful additives such as those referred to hereinbefore in a suitable carrier with low- or medium-speed diesel engine lubricating oil. As the carrier there may be employed any solvent for the product which is compatible both with the lubricating oil and with the use of the composition. The carrier may be any inert hydrocarbon solvent. The aforesaid salixarene or salixarate may be present in the concentrate in an amount in the range from 0.1 to 20% by weight.

In one embodiment, the inventive lubricating oil compositions contain a detergency improving amount of the inventive salixarene or salixarate. In one embodiment this corresponds 0.01 to 10% by weight salixarene or salixarate based on the weight of the lubricating oil composition, and in one embodiment 0.01 to 5% by weight, and in one embodiment 0.01 to 2.5% by weight based on the weight of the lubricating oil composition.

The use the salixarenes and salixarates of the invention as described hereinabove for reducing black paint in low- or medium- speed diesel engines is a further aspect of the present invention.

A further benefit of the salixarenes and salixarates of the invention is that they may be used to improve the performance of conventional diesel and gasoline detergent additives. They also stabilise such additives against thermal decomposition. Accordingly another aspect of the invention provides a composition comprising a salixarene or salixarate of the invention and a diesel or gasoline detergent. Further aspects include the use of such salixarenes and salixarates to thermally stabilise and/or enhance the detergency properties of diesel or gasoline detergents. The salixarenes and salixarates are also useful themselves as detergent additives in gasoline or diesel fuel, and may therefore be added to gasoline or diesel fuel even in the absence of another detergent. Thus, the invention, in one embodiment, is comprised of a major amount of a diesel fuel or gasoline, and a minor amount of a salixarene or salixarate. These diesel fuel and gasoline compositions typically contain 0.1 to 20% by weight of the inventive salixarenes or salixarates, and in one embodiment 3 to 11% by weight.

The invention will now be further illustrated by reference to the following Examples.

EXAMPLE 1

Preparation of Dodecyl-salicylic calix[8]arene

A 5 liter flange flask is charged with the following ingredients: 234.5 grams of dodecylphenol (0.87 moles, 1 equiv); 17.25 grams of salicylic acid (0.125 moles, 0.152 equivs); 60 grams of paraformaldehyde (2.00 moles, 2.3 equivs); 52.5 grams of 10M sodium hydroxide (40% aqueous) (0.525 moles, 0.63 equiv); and 2 kilograms of xylene (solvent)

A reaction apparatus is set up incorporating the 5 L flange flask, as flange lid and clip, overhead stirrer with paddle and PTFE stirrer gland, Dean & Stark trap and double surface condenser. The reactor contents are heated by an electric mantle/thermocouple/Eurotherm temperature controller system. The glassware from just above the mantle to just below the condenser is lagged with glass wool.

The reaction mixture is rapidly heated to 90° C. The temperature is then further increased very slowly at a rate of approximately 1° C. every 10 minutes. Water (77 ml) is collected over a period of 7 hours, at the end of which the temperature reaches 140° C. The mixture is then allowed to cool overnight before being refluxed (139° C.) for a further 2.5 hours. 100 ml of the resultant brown solution are then separated, and the xylene solvent is removed by rotary evaporator. The brown residue is then analysed by GPC and found to contain, in addition to the dodecyl-salicylic calix[8]arene, some of the six-membered ring salixarene as well as some unreacted starting material. The remaining brown solution is decanted from the catalyst residues and sufficient SN150 lubricating oil added to provide a concentrate of 50% by weight once the xylene solvent is removed by rotary evaporator. The resulting product is a clear brown solution.

EXAMPLE 2

Neutralisation of Dodecyl-salicylic Calix[8]arene

A 0.5 liter flask is charged with the following: 200 grams of the 50% solution of dodecyl-salicylic calix arene in SN150 lubricating oil from Example 1 (0.379 mol, 1 equiv); 6.2 grams of ethylene glycol (0.096 mol, 0.26 equiv); 16.2 grams of calcium hydroxide (0.213 mol, 0.56 equiv); and 100 grams of 2-ethylhexanol (solvent)

A reaction apparatus is set up incorporating the 0.5 L flange flask, a flange lid and clip, overhead stirrer with paddle and PTFE stirrer gland, splash head, double surface condenser, vacuum receiver adaptor, 250 ml receiver flask cooled by butanol/$CO_2$(s), and vacuum pump. The reactor contents are heated by an electric mantle/thermocouple/Eurotherm temperature controller system. The glassware from just above the mantle to just below the condenser is lagged with glass wool.

The mixture is stirred at 600 rpm and heated to 90° C. under a vacuum of −11 inches Hg (19 inches Hg absolute). The vacuum is then increased to −28 inches Hg (2 inches Hg absolute) for 30 minutes, before being reduced back to −11 inches of Hg (19 inches of Hg absolute) and the temperature increased to 130° C. The reaction is then held at a vacuum of −11 inches Hg (19 inches Hg absolute) and a temperature of 130° C. for 20 minutes. The temperature is raised to 200° C. and vacuum increased to −28 inches Hg (2 inches Hg absolute) to remove the solvents. The product is vacuum filtered through a sintered funnel to obtain a clear brown viscous liquid. The analysis of the product is as follows:

| TBN | 55.1 |
|---|---|
| Ca content | 1.96% |

EXAMPLE 3

Overbasing of Dodecyl-salicylic Calix[8]arene

A 1 liter flask is charged with the following: 82 grams of the 50% solution of dodecyl-salicylic calix arene in SN150 lubricating oil from Example 1 (0.155 mol, 1 equiv); 16 grams of dodecylphenol (0.059 mol, 0.38 equiv); 85 grams of tall oil fatty acid (0.302 mol, 1.9 equiv); 7 grams of ethylene glycol (0.186 mol, 1.2 equiv); 106 grams of calcium hydroxide (1.39 mol, 8.9 equiv) 40 grams of SN150 lubricating oil (diluent); and 125 grams of 2-ethylhexanol (solvent).

The mixture is stirred at 600 rpm and heated to 90° C. under a vacuum of −11 inches Hg (19 inches of Hg absolute). The vacuum is then increased to −28 inches Hg (2 inches Hg absolute) for 15 minutes, before being reduced back to −11 inches Hg (19 inches Hg absolute) and the temperature increased to 130° C. Further ethylene glycol (41 g, 0.66 mol, 4.2 equiv) is added dropwise over 10 minutes. Carbon dioxide is then pumped into the system under a vacuum of −2 inches Hg (28 inches Hg absolute) (37 g, 0.83 mol, 5.4 equiv) at the rate of 1.0 g/minute or less. Following carbonation the temperature is raised to 200° C. under a vacuum of −28 inches of Hg (2 inches Hg absolute) to remove the solvents. The product, an overbased calcium salt of dodecyl-salicylic calix[8]arene, is vacuum filtered through a sintered funnel to obtain a brown viscous liquid. The analysis of the product is as follows:

| | |
|---|---|
| TBN | 445 |
| Ca content | 15.39% |

Black Paint Performance

The compounds of the invention are evaluated for their efficacy in reducing black paint formation using the "Ashtray test". In this test the degree of sludging in residual fuel contaminated compounded oils is determined according to the following method:

Residual heavy fuel oil is dosed into the test lubricating oil, typically between 10 and 20%. The sample is thoroughly mixed until a homogenous oil is obtained. 1.5 grams of the sample is poured onto a steel test plate which is then placed in an oven for 24 hours at 100° C. After the test period has elapsed the test plate is removed from the oven and the lubricant/fuel mixture is allowed to drain off the test plate. Once the material has drained off the plate it is allowed to cool and then is visually inspected for the degree of sludge and rated as either "clean" or "dirty". Due to the variability in fuel quality the test series includes a known good performing lubricant and a poorer performing one. These materials are used as internal standards for the test and are also used to re-reference each batch of residual fuel used, with the standard good lubricant giving a clean plate when drained and the poorer performing one a highly "sludged" plate.

The lubricants employed are Shell Argina and Exxmar 30TP40. The compounds tested are the dodecyl-salicylic calixarene of Example 1, overbased dodecyl-salicylic calix[8]arene of Example 3 (also known as a "salixarate"), a linear equivalent of a salixarene comprising chains of dodecylphenol and salicylic acid groups linked by alkylene bridges, and finally a further salixarene containing two salicylic acid and six dodecylphenol units per ring (made in the same way as Example 1, but with a 3:1 molar ratio of phenol: salicylic acid instead of 7:1).

The results were as follows:

TABLE 1

| COMPOUND | STATE OF ASHTRAY |
|---|---|
| Shell Argina (control) | clean |
| Exxmar 30TP40 (control) | dirty |
| Example 1 (dodecyl-salicylic calix[8]arene) | clean |
| Example 3 (overbased Ca salt of Example 1) | clean |
| Equivalent of Example 1 but comprising 2 salicylic acid and 6 dodecylphenol units | clean |
| Linear equivalent of Example 1 (comparative) | dirty |

These results demonstrate that whereas linear compounds containing linked phenol and salicylic acid units are not effective against black paint, cyclic compounds (salixarenes) are effective, as are their overbased metal salts (salixarates).

Thermal Stability of Gasoline Diesal Detergents

The thermal stability of a conventional gasoline detergent is evaluated by thermo-gravimetric analysis, both with and without the addition of dodecyl-salicylic calix[8]arene. The detergent contains:

| | |
|---|---|
| A260, a product of BP identified as a solvent that is mainly aromatic | 31.62% |
| Mannich reaction product of Ultravis 1000 polyisobutylene substituted phenol, formaldehyde and ethylene diamine in 35% by wt of A260 | 26.14% |
| 11 mole propoxylate of dodecyl phenol | 37.71% |
| Dodecyl phenol | 4.53% |

The package containing the salixarene contains:

| | |
|---|---|
| A260, a mainly aromatic solvent ex BP | 27.15% |
| Mannich reaction product of Ultravis 1000 polyisobutylene substituted phenol, formaldehyde and ethylene diamine in 35% by wt of A260 | 26.14% |
| 11 mole propoxylate of dodecyl phenol | 37.71% |
| Dodecyl-salicylic calix[8]arene, 50% sol'n in A260 | 9.00% (equiv to 4.53% salixarene) |

The result of the thermogravimetric analysis is shown in FIG. 1, where the plot is displaced to the right (i.e., enhanced thermal stability) when the salixarene is added while maintaining the steep curve: this is highly desirable in such packages.

Performance of Gasoline Diesel Detergents

Conventional gasoline and diesel detergents are evaluated with and without the addition of the salixarene of Example 1.

Diesel engine test

A succinimide diesel detergent comprising the reaction product of a polyisobutene succinate and aminopropylimidazole is evaluated as a detergency additive in diesel fuel according to a Peugeot XUD 9 engine test. The fuel employed is RF90/6 diesel. The compounds tested are incorporated in an additive package with the following formulation:

| | |
|---|---|
| kerosene-type solvent | 35.9% by weight |
| detergent | 22.7% |
| cetane improver | 18.9% |
| lubricity agent | 9.1% |
| dodecyl phenol | 5.3% |
| demulsifier | 4.6% |
| corrosion inhibitor | 3.0% |
| antifoam | 0.5% |

The package is dosed in the fuel at 680 ml/m$^3$. The succinimide detergent is evaluated alone in the above package, and also in combination with 10% by weight of a formulation containing the dodecyl-salicylic calix[8]arene of Example 1 above (comprising 50% salixarene in Caromax 26; Caromax 26 is a high-boiling solvent having an 80% by weight aromatic content and a 20% by weight aliphatic content. The salixarene of Example 1 is also evaluated alone.

Measurements are made of percentage flow loss at 0.1 mm needle lift; the lower the figure the better the result.

TABLE 2

| ADDITIVE | % flow loss at 0.1 mm needle lift |
| --- | --- |
| No additive package | 91.3% |
| Succinimide detergent alone | 81.2% |
| Salixarene of Example 1 alone | 90.9% |
| 90% detergent, 10% salixarene | 71.1% |

These results show that the salixarene alone has essentially no detergent activity. However when incorporated at a concentration of just 10% with a onventional succinimide detergent, it promotes a substantial improvement in the performance of the detergent.

Gasoline engine (CEC) test

A gasoline detergent comprising the Mannich reaction product of a polyisobutene-substituted phenol, ethylene diamine and aldehyde is evaluated as a detergency additive according to the standard Opel Kadett engine test. The fuel employed is unleaded CEC RF 83-A-91, and the oil RL-189/1. The detergent is tested alone, and also in combination with the salixarene of Example 1 as in the diesel test above. The compounds tested are incorporated in an additive package with the following formulation:

| | |
| --- | --- |
| Paradodecylphenol/propylene oxide (11:1 mol ratio) carrier | 37.7% by weight |
| HAN 8572 (Exxon Chemicals) Aromatic solvent | 45.3% by weight |
| Total additive | 17.0% by weight |

The package is dosed in the fuel at 300 ml/m³.

Measurements are made of the inlet valve deposits.

TABLE 3

| ADDITIVE | DEPOSITS (mg) |
| --- | --- |
| No additive package | 167 |
| Mannich detergent alone | 22 |
| Salixarene of Example 1 alone | 16 |
| 90% detergent, 10% salixarene | −1 |

These results show that even alone the salixarene appears to have good detergency properties in gasoline. When combined with the conventional gasoline detergent, however, there is a significant synergistic effect.

While the invention has been explained in relation to its preferred embodiments, it is to be understood that various modifications thereof will become apparent to those skilled in the art upon reading the specification. Therefore, it is to understood that the invention disclosed herein is intended to cover such modifications as fall within the scope of the appended claims.

What is claimed is:

1. A lubricating composition, comprising: a lubricating oil and a reaction product from reacting together in a solvent and in the presence of a basic catalyst, compounds of the formulas (IIa) and (IIb)

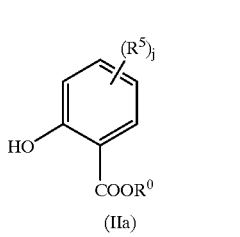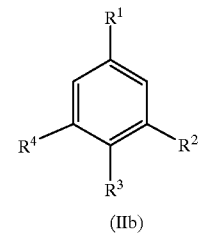

(IIa)      (IIb)

with an aldehyde of the formula O=CHR⁶, and optionally sulphur; wherein $R^0$ is H or an alkyl group of 1 to 6 carbon atoms; $R^5$ is H or an alkyl group of 1 to 60 carbon atoms; j is 1 or 2; $R^3$ is hydrogen, a hydrocarbyl or a hetero-substituted hydrocarbyl group; either $R^1$ is hydroxyl and $R^2$ and $R^4$ are independently either hydrogen, hydrocarbyl or hetero-substituted hydrocarbyl, or $R^2$ and $R^4$ are hydroxyl and $R^1$ is either hydrogen, hydrocarbyl or hetero-substituted hydrocarbyl; $R^6$ is hydrogen or hydrocarbyl; the solvent comprising at least 50% by weight of the reaction solution; the number of molar units of the compound represented by formula (IIa) being m, the number of molar units of the compound represented by formula (IIb) being n, wherein m is from 1 to 8, n is at least 1, and m+n is 2 to 20.

2. The lubricating composition of claim 1 wherein $R^6$ of the aldehyde is hydrogen.

3. The lubricating composition of claim 2 wherein $R^1$ is hydroxyl; $R^2$ and $R^4$ are hydrogen; and $R^3$ is dodecyl.

4. The lubricating composition of claim 3 wherein $R^0$ and $R^5$ are hydrogen.

5. A method for reducing black paint formation in a low-speed or medium-speed diesel engine, comprising: lubricating said engine with the lubricating composition of claim 1.

6. A fuel additive composition, comprising:
a solvent and a reaction product from reacting together in a reaction solvent and in the presence of a basic catalyst, compounds of the formulas (IIa) and (IIb)

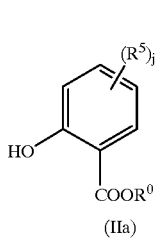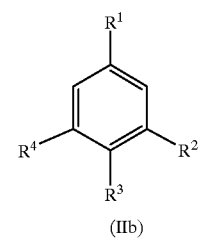

(IIa)      (IIb)

with an aldehyde of the formula O=CHR⁶, and optionally sulphur; wherein $R^0$ is H or an alkyl group of 1 to 6 carbon atoms; $R^5$ is H or an alkyl group of 1 to 60 carbon atoms; j is 1 or 2; $R^3$ is hydrogen, a hydrocarbyl or a hetero-substituted hydrocarbyl group; either $R^1$ is hydroxyl and $R^2$ and $R^4$ are independently either hydrogen, hydrocarbyl or hetero-substituted hydrocarbyl, or $R^2$ and $R^4$ are hydroxyl and $R^1$ is either hydrogen, hydrocarbyl or hetero-substituted hydrocarbyl; $R^6$ is hydrogen or hydrocarbyl; the reaction solvent comprising at least 50% by weight of the reaction solution; the number of molar units of the compound represented by formula (IIa) being m, the number of molar units of the compound represented by formula (IIb) being n, wherein m is from 1 to 8, n is at least 1, and m+n is 2 to 20.

7. A fuel composition, comprising: a major amount of a diesel fuel or a gasoline and a minor amount of the fuel additive composition of claim 6.

8. The fuel composition of claim 7, further comprising a succinimide from reaction of a polyisobutene succinate and aminopropylimidazole or a Mannich reaction product of a polyisobutene-substituted phenol, an aldehyde and ethylenediamine.

9. The fuel composition of claim 7 wherein $R^6$ of the aldehyde is hydrogen.

10. The fuel composition of claim 9 wherein $R^1$ is hydroxyl; $R^2$ and $R^4$ are hydrogen; and $R^3$ is dodecyl.

11. The fuel composition of claim 10 wherein $R^0$ and $R^5$ are hydrogen.

* * * * *